United States Patent [19]

Barberio

[11] 4,264,580
[45] Apr. 28, 1981

[54] DENTAL CREAM COMPOSITION

[76] Inventor: Giacinto G. Barberio, 195 Flixton Rd., Flixton, Urmston, Manchester, England, M31 3DN

[21] Appl. No.: 104,497

[22] Filed: Dec. 17, 1979

Related U.S. Application Data

[63] Continuation-in-part of Ser. No. 32,077, Apr. 23, 1979, abandoned.

[51] Int. Cl.³ .............................................. A61K 7/16
[52] U.S. Cl. ........................................ 424/57; 424/49; 424/56
[58] Field of Search ...................................... 424/49–58

[56] References Cited

U.S. PATENT DOCUMENTS

| | | | |
|---|---|---|---|
| 2,041,473 | 5/1936 | Janota | 424/57 |
| 2,054,742 | 9/1936 | Bibel | 424/56 |
| 2,812,284 | 11/1957 | Sanders | 424/56 |
| 3,137,632 | 6/1964 | Schiraldi | 424/57 |
| 3,692,894 | 9/1972 | Amo et al. | 424/56 |
| 3,989,813 | 11/1976 | Januszewski et al. | 424/57 |
| 4,036,950 | 7/1977 | Baines et al. | 424/57 |
| 4,123,517 | 10/1978 | Baines et al. | 424/57 |
| 4,130,636 | 12/1978 | Tomlinson | 424/57 |

FOREIGN PATENT DOCUMENTS 399917 10/1933 United Kingdom ...................... 424/56

Primary Examiner—Shep K. Rose

[57] ABSTRACT

Dental cream having a smooth texture with little tendency to form grain containing calcium carbonate polishing agent and sodium lauryl sulphate surface active agent having a broad distribution of alkyl groups containing 10–18 carbon atoms and as additive which reduces grain an alkali metal pyrophosphate or an anionic phosphate mono- and di-ester mixture.

6 Claims, No Drawings

DENTAL CREAM COMPOSITION

This application is a continuation-in-part of application Ser. No. 32,077, filed Apr. 23, 1979, now abandoned.

This invention relates to a dental cream composition having a desirable rheological character. In particular it relates to a dental cream composition of smooth texture with little tendency to form grain, particularly upon aging at low temperatures.

Calcium carbonate or chalk has long been used as a dental polishing agent. In earlier times, in spite of its effectiveness in polishing teeth, it had disadvantages in that it tended to make dental cream somewhat slimy in feel. More recently, however, grades of calcium carbonate have come into use which substantially avoid this problem.

Nevertheless, it has been observed that in dental creams containing calcium carbonate, including modern grades of the material, when the cream further contains sodium lauryl sulphate as a surface active agent, which sodium lauryl sulphate has a broad distribution of alkyl chain lengths, such as about 1–8% $C_{10}$; 40–70% $C_{12}$; 13–30% $C_{14}$; 5–16% $C_{16}$; and 0–23% $C_{18}$; grain formation does occur after storage at low temperatures, e.g., between $-7°$ to $7°$ C. This phenomenon does not generally occur when sodium lauryl sulphate having high $C_{12}$ content (e.g., 95% or more) is employed. However, since sodium lauryl sulphate of broader alkyl distribution is readily and economically commercially available and is generally compatible with many common dental cream components, it is desirable to use it.

It is an object of this invention to provide a dental cream composition comprising calcium carbonate and sodium lauryl sulphate having a broad distribution of alkyl chain lengths which composition had desirable rheological characteristics and is substantially grain free.

According to the present invention a dental cream is provided consisting essentially of a vehicle of water and humectant and a gelling agent, from 20 to 75% by weight of a polishing material wherein at least about 95% by weight of said polishing material is calcium carbonate, from 0.1 to 5% by weight of a surface active material including sodium lauryl sulphate having a broad distribution of alkyl groups, the $C_{10}$ content being about 1 to 8% by weight, the $C_{12}$ content being about 40 to 70% by weight, the $C_{14}$ content being about 13 to 30% by weight, the $C_{16}$ content being about 5 to 16% by weight and the $C_{18}$ content being about 0 to 23% by weight, and from 0.2 to 1% by weight of an additive selected from the group consisting of an $M_4$ pyrophosphate wherein M is alkali metal or ammonium and an anionic phosphate ester comprising a mixture of monoester of the formula

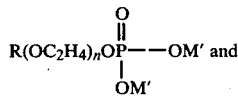

di-ester of the formula

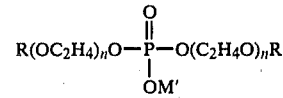

wherein M' is hydrogen, alkali metal or ammonium, R is an alkyl group of 10–20 carbon atoms and n is an integer from 1 to 6.

Calcium carbonate is available in various grades, particularly as precipitated chalk. For example, grades may have an apparent density of about 0.47–0.61 gms/cc; a flow point of about 19 to 25; a moisture loss at 105° C. of about 1 to 2%; a particle size such that at least 99.7% of the particles are finer than 74 microns (pass through U.S. 200 sieve), the median size is about 4 to 9 microns and not more than 90% are less than 18 microns; and the material is composed of calcite and aragonite in a ratio of from about 1:9 to 3:1, typically about 1:10, 1:1 or 3:1. Suitable grades are available from John and E. Sturge Ltd., Birmingham, England for instance as Sturcal H and from Johann Schaefer Kalkwerke, Diez, West Germany as Schaefer AC.

The dental cream contains about 20–75%, preferably about 40 to 55%, of polishing agent of which at least about 95% is calcium carbonate. In addition to calcium carbonate the polishing material may optionally contain up to about 5% of its content of an additional polishing agent such as dicalcium phosphate (anhydrous or dihydrate), tricalcium phosphate, dimagnesium phosphate, trimagnesium phosphate, insouble sodium metaphosphate, hydrated alumina or silica.

Sodium lauryl sulphate has long been used in dental cream compositions but it has generally been used as a "narrow cut" material in which at least 90%, even 99%, of the alkyl groups are $C_{12}$. Dental creams containing calcium carbonate and "narrow cut" sodium lauryl sulphate often do not become grainy, even upon aging at low temperatures. Commercially available grades of "narrow cut" sodium lauryl sulphate include Empicol 0045 available from Marchon Division of Albright & Wilson, Texapon K1296 available from Henkel and Cie. and Alfol 12 available from Conoco.

When sodium lauryl sulphate of broader alkyl distribution is employed, the problem of grain upon aging at low temperatures can be recognized. A particular sodium lauryl sulphate employed for the present invention contains about 3% $C_{10}$; 56% $C_{12}$; 21% $C_{14}$; 9% $C_{16}$ and 11% $C_{18}$ alkyl groups and is commercially available in the form of needles as Empicol "LZV" from Marchon Division of Albright and Wilson, Whitehaven, England. Further broad cut grades of sodium lauryl sulphate which may be employed are Tensopol SP ACL 7 from Tensia S.A., Leige, Belgium and Texapon ZH.C from Henkel and Cie., Dusseldorf, West Germany. Such grades of sodium lauryl sulphate include in their alkyl distribution about 40 to 70% $C_{12}$. More particularly, they typically have an alkyl distribution of about 1 to 8% $C_{10}$; 40 to 70% $C_{12}$, 13 to 30$C_{14}$, 5 to 16% $C_{16}$, and 0 to 23% $C_{18}$. The alkyl groups are substantially straight chain (normal).

The sodium lauryl sulphate may be prepared by means known in the art to give a product with broad alkyl distribution. "Narrow cut" sodium lauryl sulphate may be prepared from the broader cut material by fractional distillation and recrystallisation.

In addition to sodium lauryl sulphate of broad alkyl distribution, the dental cream optionally may include an additional surface active agent. Such agents may include anionic materials, for instance, water-soluble salts of higher fatty acid monoglyceride monosulphate (e.g. sodium coconut fatty acid monoglyceride monosulphate), alkyl aryl sulphonate (e.g. sodium dodecyl benzene sulphonate), higher fatty acid esters of 1,2-dihydroxy propane sulphate (e.g. sodium coconut fatty acid ester of 1,2-dihydroxy propane sulphonate) or anionic phosphate ester of the type indicated above which is also effective as an additive to reduce grain formation.

A nonionic or ampholytic surface active agent may also be present, such agents including nonionic agents such as sorbitan monostearate with approximately 60 moles of ethylene oxide, condensates of ethylene oxide with propylene glycol (available under the trademark "Pluronics") and amphoteric agents such as quaternized imidazole derivatives which are available under the trademark "Miranol" such as Miranol C2M. It is preferred that the total amount of surface active agent does not exceed about 5% by weight of the oral composition. The total surface active material content of the dental cream is about 0.1 to 5% by weight. Preferably about 1 to 2% by weight of sodium lauryl sulphate of broad alkyl distribution is present.

The additive which reduces the grain formation upon aging at low temperature, such as about $-7°$ to $7°$ C., is a phosphate material, particularly a pyrophosphate or the anionic phosphate ester mixture of mono-ester and di-ester as defined above. When the anionic phosphate ester is employed, it may also serve as part of the surface active material.

The $M_4$ pyrophosphate is an alkali metal (e.g., sodium, potassium, etc.) or ammonium salt. It may be tetrasodium pyrophosphate in its anhydrous or hydrated forms. $Na_4P_2O_7.10H_2O$ is a preferred material. The corresponding tripolyphosphate is not believed to be effective in grain reduction.

The anionic phosphate esters are mixtures of mono- and di-esters of the formulas hereinabove set forth. They are available for MoDo Kemi Aktiebolaget, formerly Berol Aktiebolaget, of Sweden under the name Berol and may include an anionic triester moiety to, as well as some nonionic portion. Berol 729 has alkyl chain lengths of 16 to 18 carbon atoms and contains series of 4 ethylene oxide units. Since the acid form of Berol 729 typically provides a completed oral preparation with a pH below 6, this material is generally used in neutralized or partially neutralized form in order to assure a pH above about 6 to the completed oral preparation.

Further anionic phosphate ester which may be used in acid or neutralized forms are Berol 525 which contains alkyl groups of 10 to 18 carbon atoms and series of 5 ethylene oxide units and Berol 513 which contains alkyl groups of 16 to 18 carbon atoms. However, use of Berol 525 may also provide a completed oral preparation with a pH below 6 and it is preferred to use it in neutralized or partially neutralized form. Further Berol anionic phosphate esters are available as Berol 521, Berol 724 and Berol 733. The weight ratio of mono-ester to di-ester may vary, typically from about 1:10 to 10:1.

The grain reduction additive is employed in amount of from 0.2 to 1% by weight, preferably fro 0.2 to 0.5%. When a dentifrice containing calcium carbonate and sodium lauryl sulphate having a broad alkyl group distribution, but not including the anti-grain additive is prepared, grain formation can be observed after aging for one month at a low temperature, such as about $-7°$ to $7°$ C., typically $4°$ C.

In the prior art there have been disclosures of dental creams in which the polishing agent contained calcium carbonate and in which sodium lauryl sulphate were present. Some of these dental creams contained a pyrophosphate salt or an anionic phosphate ester. Nevertheless, the present invention differs substantially from such disclosures.

In Example 4 of U.S. Pat. No. 3,137,632 to Schiraldi of Colgate-Palmolive Company a dentifrice is discussed which contains 50% of calcium carbonate as the only polishing agent, 2.5% of sodium lauryl sulphate, 0.25% of tetrasodium pyrophosphate and 0.3% of sodium copper chlorophyllin. In such dentrifice the low temperature grain problem could only have been recognized if a broad-cut had been used and the pyrophosphate salt omitted. The pyrophosphate salt is used to permit release of the chlorophyll material. The dentral cream of the present invention consists essentially of vehicle of humectant and water, gelling agent, polishing agent, surface active agent and anti-grain additive. Chlorophyll would not be present and, therefore, no reason exists to include pyrophosphate in accordance with the patent to Schiraldi.

In U.S. Pat. No. 2,041,473 to Janota of Victor Chemical Works a pyrophosphate salt is taught as an additive to prevent formation of a "curd" upon moistening a dentifrice powder containing a polishing agent including calcium carbonate and a soap or frothing agent. Curd formation is a phenomenon of tooth powder containing a soap type of frothing agent and is not associated with dental cream containing surface active agent such as sodium lauryl sulphate. Accordingly, one skilled in the art would not be led by the patent to Janota to introduce a pyrophosphate into such a dental cream.

In U.S. Pat. No. 4,130,636 to Tomlinson of Colgate-Palmolive Company, a dentifrice is taught wherein the surface active system includes a surfactant of the formula $R-(OCH_2CH_2)_x-OCH_2COOM$ wherein R is a $C_8-C_{18}$ alkyl chain, x is an integer 1-9 and M is a nontoxic alkali or alkaline earth metal, ammonium or $C_2$ to $C_3$ alkylol amine. Sodium lauryl sulphate may also be present as well as polishing agents including calcium carbonate and/or dicalcium phosphate. Tetrasodium pyrophosphate is employed in examples (3 and 5) in which the polishing agent is mainly dicalcium phosphate dihydrate and smaller amounts of calcium carbonate. It is well known in the art (e.g., U.S. Pat. Nos. 2,876,167 and 3,634,585 to Manahan and Manahan et al each of Colgate-Palmolive Company) that soluble pyrophosphates would be employed in such dentrifices to supress calcium ion from calcium phosphates. One skilled in the art is not led by the presence of calcium carbonate in disclosures such as those of the patent to Tomlinson to use a pyrophosphate as an additive because of the presence of calcium carbonate.

In U.S. Pat. No. 4,123,517 to Baines et al of Colgate-Palmolive Company, an anionic phosphate ester composition is taught to promote compatibility of a toothpaste containing hydrated alumina polishing material with an unlined aluminum container. Calcium carbonate may be included as minor component of the polishing material and sodium lauryl sulphate may also be present. However, a composition in which the phosphate ester is suggested for a toothpaste in which the polishing material consists essentially of calcium carbonate is not suggested by this patent.

U.S. Pat. No. 3,989,813 to Januszewski et al of Colgate-Palmolive Company includes disclosure in which a pyrophosphate may be present in a toothpaste with a bis (biguandio hexane) compound and U.S. Pat. No. 4,036,950 to Baines et al of Colgate-Palmolive Company discloses a dentrifice containing a phosphate ester composition and a cationic antibacterial agent. It is well known, for instance, from British Patent No. 825,577 to Clemow et al of International Chemical Company that sodium lauryl sulphate would be avoided in dentifrices containing such cationic materials.

U.S. Pat. No. 2,054,742 to Elbel of International Scientific Products Company, its British patent equivalent No. 399,917 to Henkel & Cie. and U.S. Pat. Nos. 2,812,284 to Sanders of Procter & Gamble and 3,692,894 to Amo et al of Kao Soap Company disclose dental compositions in which sodium lauryl sulphate having a distribution of alkyl chain lengths may be used. These patents, however, do not even lead to recognition of the low temperature grain problem, much less its solution, since one skilled in the art would not be lead to use such chain distributed sodium lauryl sulphates in a dental cream with a polishing material which is primarily calcium carbonate.

The dental cream includes as a vehicle for the polishing material, grain reduction additive and surface active material, liquids and solids proportioned to form an extrudable creamy mass of desirable consistency. In general, liquids in the dental cream will comprise chiefly water, glycerine, sorbitol, propylene glycol, or the like, including suitable mixtures thereof. It is advantageous usually to use a mixture of both water and a binder or humectant such as glycerine and/or sorbitol. It is preferred to use glycerine or mixtures of glycerine with sorbitol. The humectant is generally used in an amount between about 20 and 25%, and preferably about 22%. The total liquid content will generally be about 20 to 65% by weight of the formulation, with water being in an amount to bring the total of components to 100%.

A gelling agent is also used in dental creams such as the natural and synthetic gum and gum-like materials, e.g., Irish moss, gum tragacanth, sodium carboxymethylcellulose, polyvinyl pyrrolidone, starch and the like; all being referred to as "gum". The Irish moss and sodium carboxymethylcellulose are compatible particularly and are preferred gelling agents. The gum content is usually in an amount up to about 10% and preferably about 0.5 to 5% by weight of the formulation, with gum in an amount of about 0.9 to 1.3% especially preferred.

The total of liquid and gelling agent (gum) form the dental cream vehicle in which the other components are dispersed or dissolved.

Minor amounts of ingredients such as sweetener, flavour and, should an unlined aluminum tube be employed, stabilizer therefor, such as sodium silicate, may be employed.

The following specific example is further illustrative of the nature of the present invention but it is understood that the invention is not limited thereto. Oral compositions are prepared in the usual manner, except as indicated, and all amounts and proportions are by weight except as otherwise indicated.

EXAMPLE

The following dentifrices were prepared and placed in unlined aluminum tubes:

| Components | Parts A | B | C |
|---|---|---|---|
| Glycerine | 6.060 | 6.060 | 6.060 |
| Sodium carboxymethylcellulose | 1.200 | 1.200 | 1.200 |
| Sodium saccharin | 0.200 | 0.200 | 0.200 |
| Sodium silicate | 0.200 | 0.200 | 0.200 |
| Sorbitol (70%) | 16.000 | 16.000 | 16.000 |
| Tetrasodium pyrophosphate | — | 0.500 | — |
| Berol 513* | — | — | 0.500 |
| Deionized water | 23.433 | 22.933 | 22.933 |
| Calcium carbonate** | 42.000 | 42.000 | 42.000 |
| Sodium lauryl sulphate LZV*** | 1.807 | 1.807 | 1.807 |
| Flavour | 1.100 | 1.100 | 1.100 |
| pH | 8.65 | 9.44 | 8.20 |

*Berol 513, employed in dentifrices C is a mixture of anionic phosphate mono-esters and di-esters of the earlier indicated formulas in which the alkyl group contains 16 to 18 carbon atoms. It is a pasty material with a density of about $1.050/cm^3$ at 30° C. It is available from MoDo Kemi Aktiebolaget, of Sweden.
**The calcium carbonate employed in dentifrices A, B and C is Sturcal H chalk, available from John & E. Sturge Ltd, Birmingham, England.
***The sodium lauryl sulphate employed in dentifrices A, B & C is LZV, a broad-cut needle material available from Marchon Division of Albright and Wilson.

After aging for three months at 4° C., dentifrice A has an appearance which can be noticed as somewhat rough and grainy. On the other hand, the presence of tetrasodium pyrophosphate in dentifrice B and of Berol 513 in dentifrice C, reduces grain, such that after storage for three months at 4° C. dentifrice B is slightly rough only at the tube nozzle, but is otherwise satisfactory and indeed shiny; dentifrice C is satisfactory and shiny after storage for three months at 4° C.

Likewise, improvements are observed when tetrasodium pyrophosphate or the organic phosphate ester is present in dentifrices containing calcium carbonate available as Schaefer AC and broad-cut sodium lauryl sulphate, including LZV as well as needles of Tensapol SP ACL 7 available for Tensia, S.A., Liege, Belgium and needles of Texapon ZHC, available from Henkel and Cie., Dusseldorf, West Germany.

A grain problem also exists when the formula contains 40% calcium carbonate, such as Sturcal H and 2% dicalcium phosphate as polishing materials and broad-cut sodium lauryl sulphate, such as LZV, which problem is reduced by the presence of tetrasodium pyrophosphate or the organic phosphate ester.

I claim:

1. A dental cream consisting essentially of a vehicle of water and humectant and a gelling agent, from 20 to 75% by weight of a polishing material wherein at least about 95% by weight of said polishing material is calcium carbonate, from 0.1 to 5% by weight of a surface active material including sodium lauryl sulphate having a broad distributin of alkyl groups, the $C_{10}$ content being about 1 to 8% by weight, the $C_{12}$ content being about 40 to 70% by weight, the $C_{14}$ content being about 13 to 30% by weight, the $C_{16}$ content being about 5 to 16% by weight and the $C_{18}$ content being about 0 to 23% by weight, and from 0.2 to 1% by weight of an additive of an anionic phosphate ester comprising a mixture of mono-ester of the formula

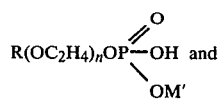

di-ester of the formula

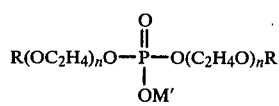

wherein M' is hydrogen, alkali metal or ammonium, R is an alkyl group of 10–20 carbon atoms and n is an integer from 1 to 60.

2. The dental cream claims in claim 1 wherein said polishing agent is present in amount of about 40–55% by weight.

3. The dental cream claims in claim 2 wherein said calcium carbonate is the only polishing agent present.

4. The dental cream claims in claim 1 wherein said sodium lauryl sulphate contains about 3% $C_{10}$; 56% $C_{12}$; 21% $C_{14}$; 9% $C_{16}$; and 11% $C_{18}$ alkyl groups.

5. The dental cream claims in claim 1 wherein said additive is present in amount of about 0.2–0.5% by weight.

6. The dental cream claims in claim 1 wherein said anionic phosphate ester mixture contains alkyl groups of 16 to 18 carbon atoms and the weight ratio of mono-ester to di-ester is from about 1:10 to about 10:1.

* * * * *

UNITED STATES PATENT AND TRADEMARK OFFICE
CERTIFICATE OF CORRECTION

PATENT NO. : 4,264,580
DATED : April 28, 1981
INVENTOR(S) : Giacinto G. Barbario It is certified that error appears in the above-identified patent and that said Letters Patent are hereby corrected as shown below:

On the cover page, left column after line 4 insert

--(73) Assignee: Colgate-Palmolive Company, New York, NY.--

Signed and Sealed this

Fourth Day of August 1981

[SEAL]

Attest:

Attesting Officer

GERALD J. MOSSINGHOFF

Commissioner of Patents and Trademarks